(12) United States Patent
Adams et al.

(10) Patent No.: US 10,743,973 B2
(45) Date of Patent: *Aug. 18, 2020

(54) TEMPORAL MANDIBLE DATA CAPTURE ANALYSIS AND RECOMMENDATION

(71) Applicant: International Business Machines Corporation, Armonk, NY (US)

(72) Inventors: Ebony C. Adams, Austin, TX (US); Ching-Yun Chao, Austin, TX (US); Christian Compton, Austin, TX (US); Jeremy R. Fox, Georgetown, TX (US); Manjunath Ravi, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 326 days.

This patent is subject to a terminal disclaimer.

(21) Appl. No.: 15/842,075

(22) Filed: Dec. 14, 2017

(65) Prior Publication Data
US 2019/0133731 A1    May 9, 2019

Related U.S. Application Data

(63) Continuation of application No. 15/805,477, filed on Nov. 7, 2017.

(51) Int. Cl.
*A61B 5/00* (2006.01)
*A61C 19/045* (2006.01)
*A61B 5/11* (2006.01)
*G06F 16/903* (2019.01)

(52) U.S. Cl.
CPC .......... *A61C 19/045* (2013.01); *A61B 5/1121* (2013.01); *A61B 5/4557* (2013.01); *A61B 5/746* (2013.01); *G06F 16/90335* (2019.01)

(58) Field of Classification Search
CPC .......... A61B 5/00; A61B 5/4557; A61B 5/11; A61B 5/7282; A61B 5/6814; A61B 5/0022; A61B 5/6831; A61B 2562/0219; A61B 2505/07; G16H 40/67
See application file for complete search history.

(56) References Cited

U.S. PATENT DOCUMENTS

| 9,029,410 | B2 | 5/2015 | Heresco-Levy et al. |
|---|---|---|---|
| 9,421,074 | B2 | 8/2016 | Sachdeva et al. |
| 9,561,088 | B2 | 2/2017 | Sachdeva et al. |
| 2014/0243350 | A1 | 8/2014 | Hansen et al. |

(Continued)

FOREIGN PATENT DOCUMENTS

RU    2628064 C2    8/2017

OTHER PUBLICATIONS

Eric J. Messersmith, USPTO Office Action, U.S. Appl. No. 15/805,477, dated Sep. 26, 2019, 13 pages.

(Continued)

*Primary Examiner* — Eric J Messersmith
(74) *Attorney, Agent, or Firm* — Scott S. Dobson; Hunter E. Webb; Keohane & D'Alessandro, PLLC

(57) ABSTRACT

Approaches presented herein enable performing an oral health diagnosis of a user using an oral monitoring device fixed in the oral cavity. Specifically, an oral monitoring device collects jaw movement data as a user goes about daily living. An oral healthcare analysis is performed comparing current measurement data against abnormality classifications to identify abnormal jaw movement. If an abnormality is identified, an oral healthcare professional can be notified.

6 Claims, 7 Drawing Sheets

(56) References Cited

U.S. PATENT DOCUMENTS

2016/0367188 A1  12/2016  Malik et al.
2017/0265801 A1   9/2017  Patwa et al.

OTHER PUBLICATIONS

D.J. Ostry et al., "Human Jaw Movement in Mastication and Speech", Archs oral Biol., vol. 34, No. 9, 1989, pp. 685-693.

Authors et al.: Disclosed Anonymously, "Oral Cavity Sound Reporducer and Inducer", IP.com No. IPCOM000240582D, IP.com Electronic Publication Date: Feb. 10, 2015, 3 pages.

Authors: Siemens et al., "A Multiple Instance Learning Based Self Learning Approach to Reduce Human Effort in Marking Regions of Interest in Imaging Applications", IP.com No. IPCOM000213368D, IP.com Electronic Publication Date: Dec. 13, 2011, Copyright: Siemens AG 2011, 3 pages.

Jung Ho Kim, "Development of wireless bruxism monitoring device based on pressure-sensitive polymer", Printed Sep. 26, 2017, 18 pages.

Cheng-Yuan Li, "Sensor-Embedded Teeth for Oral Activity Recognition", ISWC '13, Sep. 9-12, 2013, Zurich, Switzerland, pp. 41-44.

Eric J. Messersmith, USPTO Notice of Allowance and Fee(s) Due, U.S. Appl. No. 15/805,477, dated Jan. 6, 2020, 8 pages.

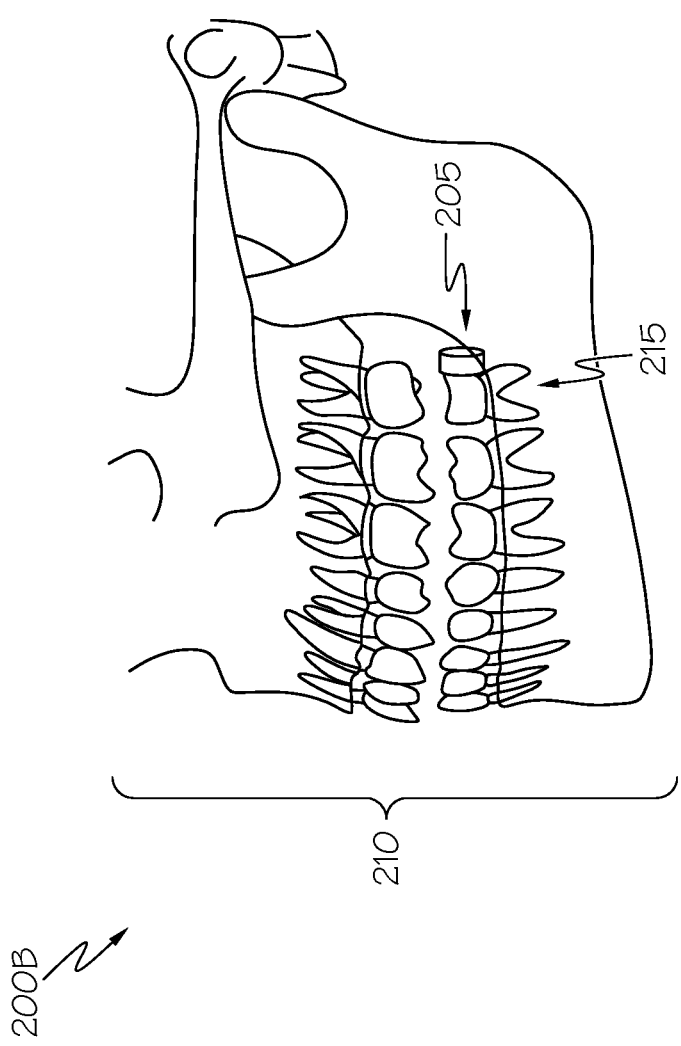

TEMPORAL MANDIBLE DATA CAPTURE ANALYSIS AND RECOMMENDATION

CROSS-REFERENCE TO RELATED APPLICATIONS

The present patent document is a continuation of U.S. patent application Ser. No. 15/805,477, filed Nov. 7, 2017, entitled "TEMPORAL MANDIBLE DATA CAPTURE ANALYSIS AND RECOMMENDATION", the disclosure of which is incorporated herein by reference.

TECHNICAL FIELD

This invention relates generally to oral health monitoring. The invention is drawn, more specifically, to gathering measurement data over time of the movement of a user's jaw, performing an oral health diagnostic on the measurement data by comparing the user's jaw movement to a set of abnormality classifications, and generating an oral healthcare insight based on the results of the oral health diagnostic.

BACKGROUND

Abnormal jaw movement and abnormal repetition of jaw movements are associated with mouth, teeth, and jaw pathologies. Jaw movement abnormalities such as bruxism (teeth grinding) may lead to tooth decline or muscular tension, which may lead to stiff jaw or headaches and even to changes in the structural features of the face. Physical impacts, such as car accidents, may cause jaw movement difficulties. Further, problems in the temporomandibular joint of the jaw may cause pain and other discomforts and disease manifestations. Monitoring of jaw movement may assist in identifying and treating jaw abnormalities.

SUMMARY

In general, embodiments described herein provide approaches for performing oral health diagnostics of a user utilizing data from an oral monitoring device. Specifically, jaw movement data are aggregated temporally to diagnose, treat, and monitor disorders of the jaw and mouth. An oral monitoring device having a sensor capable of collecting jaw movement data (e.g., accelerometer, gyroscope, etc.) is installed in the oral cavity of a user over time to determine abnormalities in jaw movement as the user goes about daily life. Analysis of these data using cognitive computing and machine learning abilities allows identification of jaw movement outliers falling within abnormality classifications for the individual wearing the sensor. Jaw movement abnormalities may additionally be identified when the individual's data are compared to data from a similarly-situated population by employing, for example, crowd-sourced data. Cognitive computing and machine learning abilities may further provide cognitive system recommendations to an oral health professional concerning diagnosis and possible treatment of the individual as well as suggestions concerning underlying causes of the observed jaw abnormalities, which may prompt further investigation by the oral health professional.

By comparing current measurement data against a set of abnormality classifications, abnormal jaw movement may be identified. If measurements fall within an abnormality classification or exceed a predefined permissible threshold of expected results, an oral healthcare professional may be notified. An oral health care professional presented with these data may predict or indicate an oral health issue and may provide treatment or corrective suggestions.

One non-limiting aspect of the present invention includes a computer-implemented method for identifying jaw abnormalities in an individual, comprising: collecting jaw movement data of the user over a period of time from an oral monitoring device affixed within the oral cavity of the user, retrieving a set of abnormality classifications from a database, performing a diagnostic of the jaw movement data by comparing the jaw movement data and the set of abnormality classifications to asses an abnormality in jaw movement and identifying an abnormality in jaw movement in the individual based on the diagnostic.

In an embodiment, performing a diagnostic of the jaw movement data by comparing the jaw movement data, the set of abnormality classifications, and jaw movement data aggregated across at least one population of users to asses an abnormality in jaw movement, and identifying a jaw abnormality of the user based on the diagnostic. In another embodiment, the computer-implemented method additionally compares the identified jaw abnormality to similar abnormalities in jaw movements of a population of users similar to the user and returns diagnosis and treatment recommendations within a specified confidence interval, weighted by effectiveness, based on treatments and success with the similar abnormalities. In a further embodiment, treatment options are identified using cognitive data analysis. Yet another embodiment provides generating an alert to the user or the user's oral healthcare professional, or both, in response to identifying an abnormality. In a non-limiting embodiment, the jaw movement data may be from an accelerometer or gyroscope. In another non-limiting embodiment, the jaw movement data may include rotational movement in the traverse plane, excessive lateral jaw movement, motion in three planes, rotational movement over an extended period of time, mandible-stroke frequency, and/or overall dynamic body acceleration of the jaw.

Another non-limiting aspect of the present invention includes an oral monitoring system for identifying at least one jaw abnormality of a user, the system including an oral monitoring device having an outer housing, the outer housing being affixed within an oral cavity of the user, a set of sensors located in the oral monitoring device that collects jaw movement data of the user, a network adapter located in the oral monitoring device that forwards the jaw movement data of the user to a diagnosis computer system that performs a diagnostic that compares the jaw movement data with a set of abnormality classifications in a database and identifies a jaw abnormality of the user based on the diagnostic.

Yet another non-limiting aspect of the present invention includes a computer program product for performing a health analysis of a user, the computer program product comprising a computer readable storage device, and program instructions stored on the computer readable storage device, to: collect jaw movement data for the user over a period of time from an oral monitoring device affixed within the oral cavity of the user, retrieve a set of abnormality classifications from a database, perform a diagnostic of the jaw movement data by comparing the jaw movement data and the set of abnormality classifications to asses an abnormality in jaw movement and, identify a jaw abnormality of the user based on the diagnostic.

Yet still another non-limiting aspect of the present invention includes a method for facilitating diagnosis of abnormal jaw movement of an individual, comprising: providing a computer infrastructure that includes at least one computer device that operates to perform the steps of: collect jaw movement data for the user over a period of time from an oral monitoring device affixed within the oral cavity of the user; retrieve a set of abnormality classifications from a database; perform a diagnostic of the jaw movement data by comparing the jaw movement data and the set of abnormality classifications to asses an abnormality in jaw movement; and identify a jaw abnormality of the user based on the diagnostic.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings in which:

FIG. 2B shows an example oral monitoring device diagram 200B including oral monitoring device 205 affixed to rear molar 215 within oral cavity 210 according to illustrative embodiments;

Figure 1:
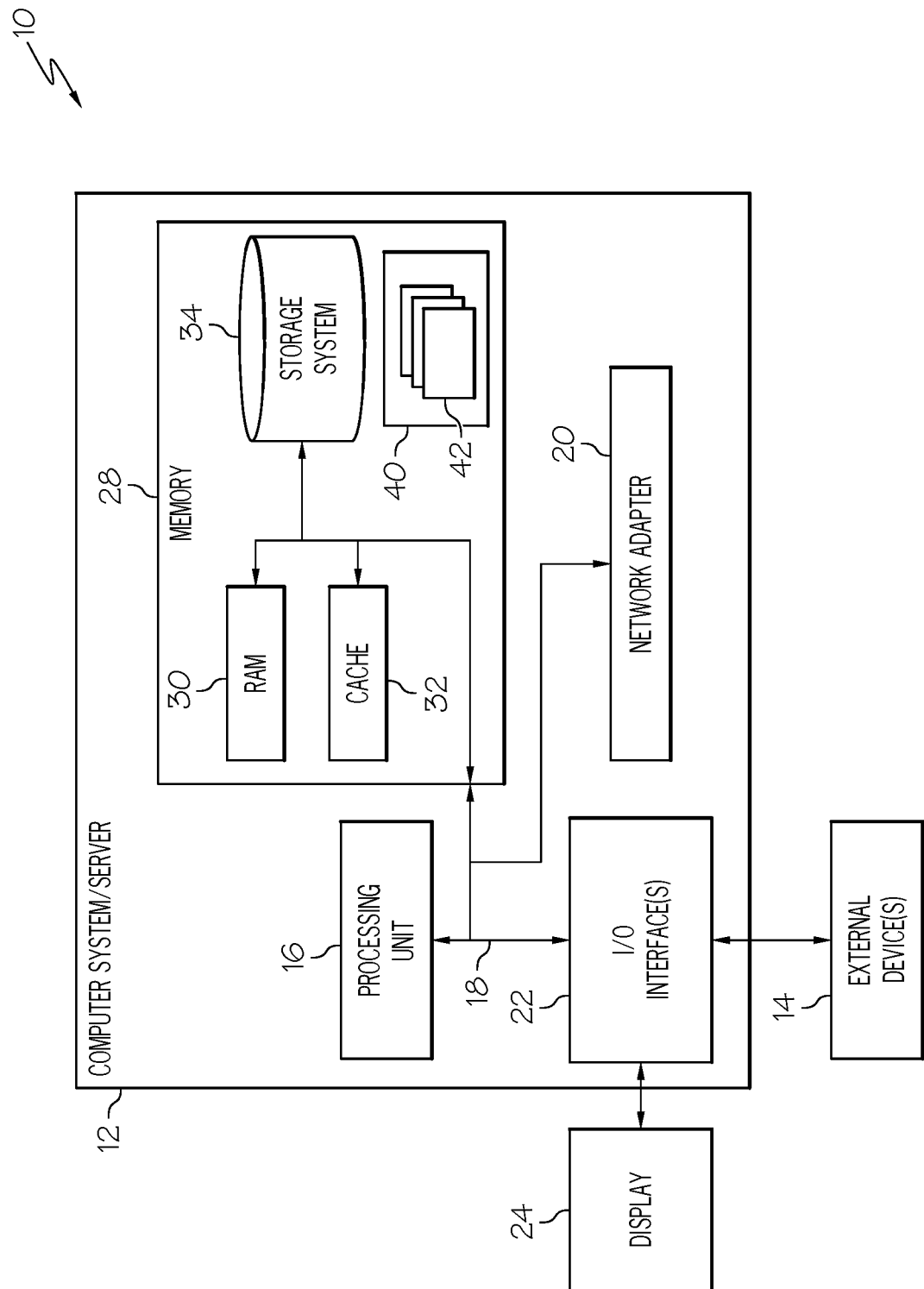
FIG. 1 shows an architecture 10 in which the present invention may be implemented according to illustrative embodiments.

The drawings are not necessarily to scale. The drawings are merely representations, not intended to portray specific parameters of the invention. The drawings are intended to depict only typical embodiments of the invention, and therefore should not be considered as limiting in scope. In the drawings, like numbering represents like elements.

DETAILED DESCRIPTION

Illustrative embodiments will now be described more fully herein with reference to the accompanying drawings, in which illustrative embodiments are shown. It will be appreciated that this disclosure may be embodied in many different forms and should not be construed as limited to the illustrative embodiments set forth herein. Rather, these embodiments are provided so that this disclosure will be thorough and complete and will fully convey the scope of this disclosure to those skilled in the art.

Furthermore, the terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. Furthermore, similar elements in different figures may be assigned similar element numbers. The term "set" is intended to mean a quantity of at least one. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

Unless specifically stated otherwise, it may be appreciated that terms such as "processing," "detecting," "determining," "evaluating," "receiving," or the like, refer to the action and/or processes of a computer or computing system, or similar electronic data center device, that manipulates and/or transforms data represented as physical quantities (e.g., electronic) within the computing system's registers and/or memories into other data similarly represented as physical quantities within the computing system's memories, registers or other such information storage, transmission, or viewing devices. The embodiments are not limited in this context.

Within the current invention, it has been discovered that collection of jaw movement data aggregated temporally allows diagnosis, treatment, and monitoring of disorders of the jaw. In a non-limiting aspect of the invention, an oral monitoring device having at least one sensor is installed in the oral cavity to collect data over an extended period of time to determine any abnormalities in movement while a patient engages in daily life. Analyzing these data using advanced cognitive computing and machine learning abilities allows identification of outliers for both the individual within her/his own data set and for the individual as compared to an aggregated data set of a population. Diagnostics on these data provides oral health care professionals cognitive system recommendations pertaining to diagnosis, treatment, and underlying causes of oral disorders that may be investigated.

Data collected from an oral monitoring device over time provide classification of jaw movements and available analysis of abnormal activity over the course of general daily activities. Analysis of the collected information is beneficial in proactively addressing dental health issues and provides a large sample size, which can help dental professionals make diagnoses and undertake treatments. Aggregating and comparing conditions and treatment options across similar populations additionally provides increased confidence in treatment recommendations. In addition, crowdsourcing an ever-larger sample size of collected data provides a baseline for model analysis of normal distribution and identification of pathologies correlated with statistical outliers from expected results and inliers within an abnormality classification.

Dental cleanings, typically performed twice per year, only provide an instantaneous analysis of the oral health of a patient. The lack of oral health data beyond dental checkups means that underlying medical issues may go undiagnosed and untreated until a major medical procedure is required; or go undiagnosed and untreated because the pathology is not easily detectable in a current clinical setting. The inventors have discovered certain deficiencies in the current art concerning absence of health care data between visits to the doctor and/or dental cleanings and absence of data accessed during daily living of patients. Aspects of the current invention provide solutions for one or more of these gaps in oral health care data and diagnoses.

Smart objects are devices that collect data with minimal interference in the daily lives of users. These wearable objects are becoming ever more popular. In an increasingly health-conscious and aging culture there is both desire and willingness to collect health data through wearable technology, which can allow users and their health care providers to monitor user health during daily living and provide predictions and diagnoses from cognitive data analysis. Non-limiting embodiments of the present invention provide an oral monitoring device, which can include one or more sensors (e.g., as an accelerometer, gyroscope, etc.) noninvasively and, in an embodiment, removably affixed in the oral cavity of a user during daily activity. This kind of smart object providing insight into daily oral health can be useful.

People increasingly want to monitor and improve their health without taking a trip to a doctor's office. Using sensory data to provide jaw movement data over time, non-limiting embodiments of the present invention are able to identify abnormal jaw movement, identify oral health ailments, predict forthcoming oral health ailments, and show improvement with changes in jaw movement over time—without being disruptive of everyday activity. The oral monitoring device described herein may be used, for example, prior to or following a visit to a dentist. In addition, when data are collected and aggregated from multiple users representing a large pool of individuals, data scientists and oral healthcare providers may be able to distinguish valuable patterns in jaw movement that give insight into oral health aliments and their causes and improve treatment plans.

As stated above, embodiments described herein provide approaches for performing an oral health diagnosis of an individual using an oral monitoring device. Specifically, an oral monitoring device having one or more sensors capable of collecting accelerometric, gyroscopic, temperature, and/or other data can be removably affixed within the oral cavity, such as to a rear molar on the mandible, so as to be noninvasive. The one or more sensors can be capable of tracking motion in three planes and/or rotational movement over an extended period of time, using one or more accelerometers, gyroscopes, etc., to cognitively analyze jaw movement temporally to detect abnormalities. Recordings of acceleration, position, force, etc., from mandibular and/or maxillary movement can be analyzed against a database of abnormality classifications allowing identification of jaw abnormalities.

Referring now to FIG. 1, a computerized implementation 10 of an embodiment for performing an oral health diagnosis using measured jaw movement data to provide a health care insight (such as, for example, identifying a jaw movement anomaly and providing a treatment or diagnosis recommendation to an oral healthcare provider) will be shown and described. Computerized implementation 10 is only one example of a suitable implementation and is not intended to suggest any limitation as to the scope of use or functionality of embodiments of the invention described herein. Regardless, computerized implementation 10 is capable of being implemented and/or performing any of the functionality set forth hereinabove.

In computerized implementation 10, there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

This is intended to demonstrate, among other things, that the present invention could be implemented within a network environment (e.g., the Internet, a wide area network (WAN), a local area network (LAN), a virtual private network (VPN), etc.), a cloud-computing environment, a cellular network, or implemented on a stand-alone computer system. Communication throughout the network can occur via any combination of various types of communication links. For example, the communication links can comprise addressable connections that may utilize any combination of wired and/or wireless transmission methods. Where communications occur via the Internet, connectivity can be provided by conventional TCP/IP sockets-based protocol, and an Internet service provider can be used to establish connectivity to the Internet. Still yet, computer system 12 is intended to demonstrate that some or all of the components of implementation 10 can be deployed, managed, serviced, etc., by a service provider who offers to implement, deploy, and/or perform the functions of the present invention for others.

Computer system 12 is intended to represent any type of computer system that may be implemented in deploying/realizing the teachings recited herein. Computer system 12 may be described in the general context of computer system executable instructions, such as program modules, being executed by a computer system. Generally, program modules may include routines, programs, objects, components, logic, data structures, and so on, that perform particular tasks or implement particular abstract data types. In this particular example, computer system 12 represents an illustrative system for performing an oral health diagnosis using jaw movement data to identify a jaw movement anomaly and provide a treatment or diagnosis recommendation to an oral healthcare provider. It should be understood that any other computers implemented under the present invention may have different components/software, but can perform similar functions. Computer system 12, as noted above in a non-limiting example, may be a server.

Computer system 12 in computerized implementation 10 is shown in the form of a general-purpose computing device. The components of computer system 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Processing unit 16 refers, generally, to any apparatus that performs logic operations, computational tasks, control functions, etc. A processor may include one or more subsystems, components, and/or other processors. A processor will typically include various logic components that operate using a clock signal to latch data, advance logic states, synchronize computations and logic operations, and/or provide other timing functions. During operation, processing unit 16 collects and routes signals representing inputs and outputs between external devices 14 and input devices (not shown). The signals can be transmitted over a LAN and/or a WAN (e.g., T1, T3, 56 kb, X.25), broadband connections (ISDN, Frame Relay, ATM), wireless links (802.11, Bluetooth, etc.), and so on. In some embodiments, the signals may be encrypted using, for example, trusted key-pair encryption. Different systems may transmit information using different communication pathways, such as Ethernet or wireless networks, direct serial or parallel connections, USB, Firewire®, Bluetooth®, or other proprietary interfaces. (Firewire is a registered trademark of Apple Computer, Inc. Bluetooth is a registered trademark of Bluetooth Special Interest Group (SIG)).

In general, processing unit 16 executes computer program code, such as program code for performing an oral health diagnosis using jaw movement data to identify a jaw movement abnormality and provide a treatment or diagnosis recommendation which is stored in memory 28, storage system 34, and/or program/utility 40. While executing computer program code, processing unit 16 can read and/or write data to/from memory 28, storage system 34, and program/utility 40.

Computer system 12 typically includes a variety of computer system readable media. Such media may be any available media that is accessible by computer system 12. Such media may include both volatile and non-volatile media and may include both removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media, (e.g., VCRs, DVRs, RAID arrays, USB hard drives, optical disk recorders, flash storage devices, and/or any other data processing and storage elements for storing and/or processing data). By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and/or an optical disk drive for reading from or writing to a removable, non-volatile optical disk such as a CD-ROM, DVD-ROM, or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program code embodied on a computer readable medium may be transmitted using any appropriate medium including, but not limited to, wireless, wireline, optical fiber cable, radio-frequency (RF), etc., or any suitable combination of the foregoing.

Program/utility 40, having a set (at least one) of program modules 42, may be stored in memory 28 by way of example, and not limitation. Memory 28 may also have an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a consumer to interact with computer system/server 12; and/or any devices (e.g., network card, modem, etc.) that enable computer system/server 12 to communicate with one or more other computing devices. Such communication can occur via I/O interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that, although not shown, other hardware and/or software components could be used in conjunction with computer system/server 12. Examples include, and are not limited to: microcode, device drivers, redundant processing units, external disk drive arrays, RAID systems, tape drives, and data archival storage systems, etc.

Figure 2A:
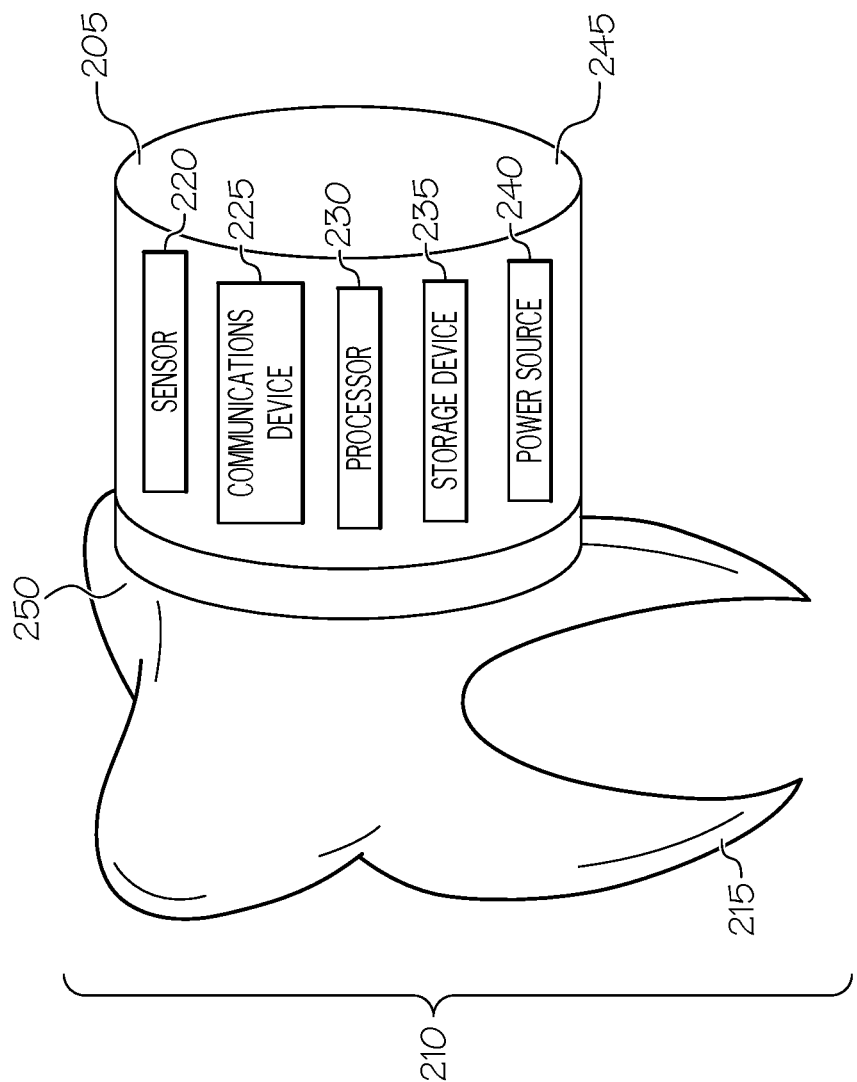
FIG. 2A shows an example oral monitoring device diagram 200A including oral monitoring device 205 affixed to rear molar 215 within oral cavity 210 according to illustrative embodiments.

Referring now to FIG. 2A, an example oral monitoring device 205 is shown in oral monitoring device diagram 200A according to an embodiment. As shown, oral monitoring device 205 is attached to rear molar 215 within oral cavity 210. Oral monitoring device 205 includes sensor 220 (e.g., accelerometer, gyroscope, thermometer, etc.) communications device 225 (e.g., wireless), processor 230 (e.g., logic device), storage device 235 (e.g., flash memory, etc.), and power source 240 (e.g., battery, capacitor, etc.). Outer housing 245 of oral monitoring device 205 may be made of ceramic, resin, porcelain, thermo-plastic polymers, acrylic, zirconium, stainless steel, metal alloy, or any other appropriate material capable of housing a monitoring device and power source. In a non-limiting embodiment, outer housing 245 of oral monitoring device 205 may be constructed from material capable of allowing wireless communication signals to be transmitted and/or received from an external communication device.

Affixing mechanism 250 affixes oral monitoring device 205, for example, to rear molar 215. Oral monitoring device 205 may be affixed on the surface of any tooth, on the top of any tooth, on the side of any tooth, between any teeth, or behind a rear molar. Oral monitoring device 205 may be affixed or placed anywhere in the oral cavity such that it may collect motion data. In a non-limiting embodiment, oral monitoring device 205 may be affixed in the socket of a removed wisdom tooth. Affixing mechanism 250 may act by any known or hereafter known oral affixing mechanism. As an example, affixing mechanism 250 may be an oral adhesive, such as, and not limited to, oral cement. Oral cement may include and is not limited to: low-strength base cements, such as hydroxide applied with zinc oxide; glass and hybrid ionomers, such as aluminosilicate glass combined with polyacrylic acid in water or dilute tartaric acid; zinc oxide-eugenol (IRM) cements, such as, oxide combined with eugenol (and phenyl propene) and plasticizing olive oil; and zinc phosphate, such as zinc oxide powder combined with phosphoric acid. Affixing mechanism 250 may likewise be any mechanical fastening mechanism including, and not limited to, a strap, a retainer, an appliance, a tooth cap, a screw, etc.

Oral monitoring device 205 can comprise one or more sensor(s) 220. Sensor 220 may include: an accelerometer, a gyroscope, a thermometer, and/or any other type of sensor contemplated by one of skill in the art now and hereafter.

Communications device 225 can be any communications device known in the art now and hereafter including, for example, any combination of wired and/or wireless transmission methods such as those described for I/O interfaces 22. Capacity of oral monitoring device 205 to transmit data continually over a network protocol via communications device 225, when available, may allow computer system 12 to undergo real-time analysis of data provided from oral monitoring device 205. Capacity of oral monitoring device 205 to transmit data in real time and avoid storing data over longer periods of time may allow slower use of power and may allow a non-limiting embodiment to have a longer running power source.

Processor 230, generally, may be any apparatus that performs logic operations, computational tasks, control functions, etc., as described, for example, for processor 16. In a non-limiting embodiment, oral monitoring device 205 may contain processor 16 within computer system 12.

Storage device 235 may be any storage device known in the art now and hereafter including, for example, storage devices described for storage system 34. Oral monitoring device 205 may have the capacity to store and/or transmit data over a network protocol. Storage capacity in storage device 235 may, for example, provide oral monitoring device 205 with the ability to continue collecting data even when not connected to an external storage system through a wireless or other network connection.

Power source 240 may be any power source known to one of skill in the art now and hereafter, including, for example, a battery, a capacitor, an ultrasonic generator, an inductive coupling generator, a thermoelectric generator, any biology-enabled generator, etc.

Oral monitoring device 205 may include a group of sensors used for collecting and processing electromagnetic signals such as, for example, accelerometric data. Oral monitoring device 205 may be of any size capable of being affixed in the oral cavity. In a typical embodiment, oral monitoring device 205 is sufficiently small not to interfere with daily living of an individual when affixed to the surface of a rear molar on the mandible or maxillary.

Referring now to FIG. 2B, an example affixing of oral monitoring device 205 within oral cavity diagram 200B is shown according to an embodiment. As shown, oral monitoring device 205 may be affixed within oral cavity 210 using any method known in the art now or hereafter. Oral monitoring device 205 may be permanently or removably affixed to any tooth (e.g., molar tooth 215), may be permanently or removably affixed to the gums, may be permanently or removably affixed to the jaw, or may be embedded in any tooth or any part of the jaw.

In an embodiment, multiple oral monitoring devices 205 may be affixed within oral cavity 210. In a non-limiting embodiment, four oral monitoring devices 205 may be affixed within oral cavity 210 with one oral monitoring device 205 being affixed to the right mandible, one oral monitoring device 205 being affixed to the left mandible, one oral monitoring device 205 being affixed to the right maxillary, and one oral monitoring device 205 being affixed to the left maxillary. To this extent, embodiments of the invention may include one, two, three, four, five, six, seven, eight, or more oral monitoring devices 205 in different positions of oral cavity 210. Multiple oral monitoring devices 205 may allow, for example, comparison of left and right and mandible and maxillary jaw movements in the oral cavity.

One non-limiting example provides a method to collect and measure an individual human's unique jaw movements. Therein, an oral monitoring device capable of collecting accelerometric data is adhered to a rear molar on the mandible so as to be noninvasive. The device tracks motion in three planes and rotational movement over an extended period of time, using accelerometers. Recordings of acceleration in jaw movement, including chewing, allows, among other things, quantification of the rate at which the human is expending energy during chewing. Measurements may include, and are not limited to, determination of mandible-stroke frequency and overall dynamic body acceleration of the jaw.

In a non-limiting embodiment, the oral monitoring device may be connected to an amplifier to amplify the external signal of the sensor. In another non-limiting embodiment, the device may include sensor 220 (such as an accelerometer) that is biology enabled. In another non-limiting embodiment, the device is capable of transmitting data via a network protocol in live time. In another non-limiting embodiment, the device is capable of notifying the user of abnormal activity in real time. In another non-limiting embodiment, the device is capable of retaining data until the device is removed from the oral cavity for data analysis. Removal may be undertaken, as a non-limiting example, during a dental screening.

Figure 3:
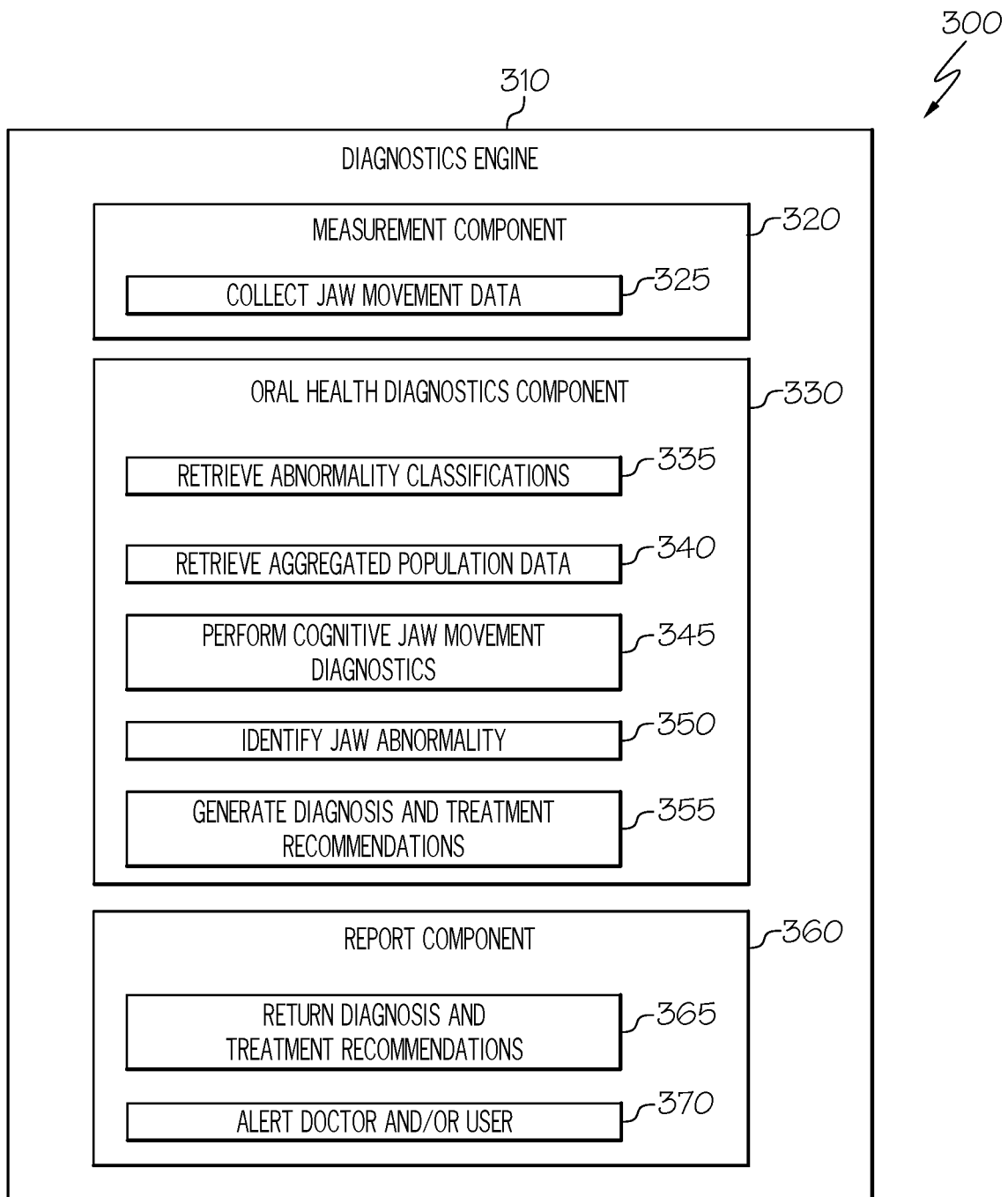
FIG. 3 shows a block diagram 300 that illustrates a system according to illustrative embodiments.

Referring now to FIG. 3, a block diagram 300 describing the functionality discussed herein according to an embodiment of the present invention is shown. It is understood that the teachings recited herein may be practiced within any type of computing environment (e.g., computer system 12). To this extent, the teachings recited herein may be practiced within a stand-alone computer system or within a networked computing environment (e.g., a client-server environment, peer-to-peer environment, distributed computing environment, cloud computing environment, and/or the like). If the teachings recited herein are practiced within a networked computing environment, each physical server need not have a diagnostics engine (hereinafter "system 310"). Rather, system 310 could be loaded on a server or server-capable device that communicates (e.g., wirelessly) with the physical server. Regardless, as depicted, system 310 can be implemented as program/utility 40 on computer system 12 of FIG. 1 and can enable the functions recited herein. It is further understood that system 310 may be incorporated within or work in conjunction with any type of system that receives, processes, and/or executes commands with respect to information technology (IT) resources in a networked computing environment. Such other system(s) have not been shown in FIG. 3 for brevity purposes.

Figure 4:
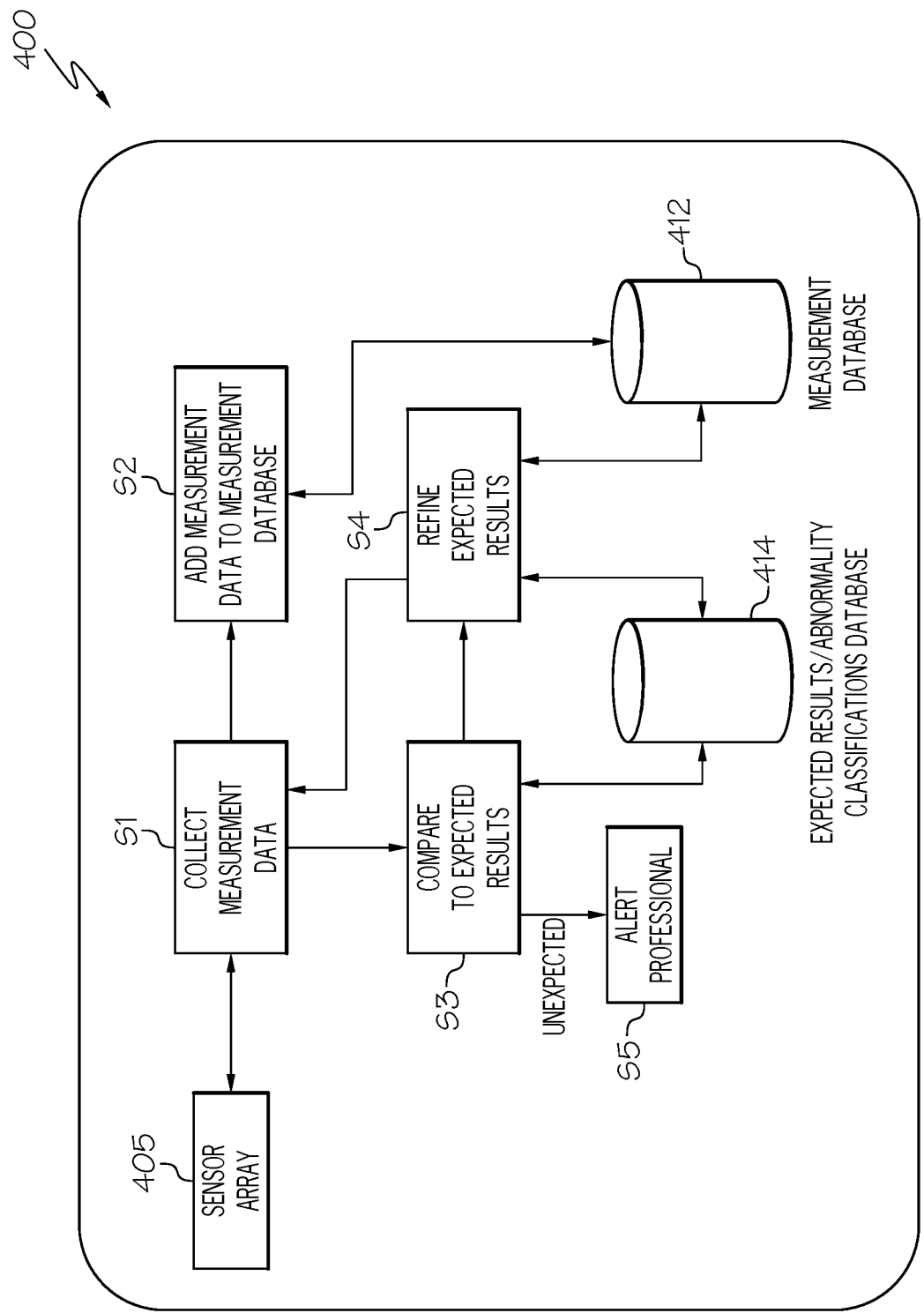
FIG. 4 shows a flow diagram 400 for performing an oral health diagnostic using an oral monitoring device to generate an oral healthcare alert according to illustrative embodiments.

Referring now to FIG. 4 in conjunction with FIGS. 1-3, an example flow diagram 400 for performing an oral health diagnosis according to an embodiment of the invention is shown. At S1, oral monitoring device(s) 205 as sensor array 405 collects measurement data as a user goes about daily life. As mentioned earlier, measurement data can include any objective measurements used for quantitative jaw movement analysis including, but not limited to, a user identity, pressure of bite, rate of chewing and/or grinding, three-dimensional motion, time of various three-dimensional motions, overbite, underbite, crossbite, jaw alignment, temporomandibular joint motion and setting, numerical description of pressure, motion, rate, and the like.

Measurement component 320 of system 310, as executed by computer system/server 12, is configured to receive any measurement data, such as jaw movement data 325, collected by oral monitoring device 205. For example, oral monitoring device 205 may be designed to transmit data measurements to measurement component 320 via data transmission. Data transmission may be performed, either by wire or wirelessly, in accordance with appropriate transmission principles known in the art, and data encryption may be employed if desired. Measurement data may be periodically received by measurement component 320 (e.g., as user jaw motion occurs during daily life), or may be pushed to measurement component 320 (e.g., nightly), or may be pulled to measurement component 320 (e.g., periodically, dynamically, randomly), or so forth. At S2, measurement data may be accumulated over a period of time and stored in measurement database 412 in order to accumulate quantitative jaw movement analysis data to derive a historical jaw movement pattern of a particular user.

Oral health diagnostics component 330 of system 310, as executed by computer system/server 12, is configured to analyze measurement data collected by measurement component 320 to assess a user's jaw movements in order to transform raw measurement data into oral healthcare insights such as trends, patterns, and deviations. Assessing a user's jaw movements can be useful for identifying particular areas of impairment and defects affecting oral health including potential jaw pathologies. For example, rotational movement in the transverse plane may indicate problems with the temporomandibular joint on one side of the jaw. However, assessing a user's jaw movement is not only useful for identifying physical impairments and oral diseases, but is also useful for monitoring the progress of rehabilitative measures and the recovery of a user after an injury or surgical procedure.

To assess a user's jaw movement pattern over time, at S3, current measurement data acquired by measurement component 320 and expected results (or abnormality classifications) stored in expected results/abnormality classifications database 414 are made accessible to oral health diagnostics component 330 to execute a comparison and determine whether there is a deviation exceeding a predefined permissible threshold or falling within an abnormality classification (or expected result) from retrieve abnormality classifications 335. Expected results and abnormality classifications may be derived from a user's historical measurement data, historical measurements of other individuals, medical studies, medical trials, medical research, medical professionals, and/or inputs from data scientists, among others. Expected results can be used to provide an acceptable jaw movement pattern range (e.g., chewing, grinding, motion in the transverse plane, balance, etc.) for a particular user. Abnormality classifications may be used to identify unacceptable jaw movement patterns (such as, for example, bruxism, malocclusion, or hypermobility).

Oral health diagnostics component 330, employing, for example, perform cognitive jaw movement diagnostics 345, determines whether any measurements of the user's current measurement data exceed a predefined permissible threshold when compared to expected results or whether any measurements of the user's current measurement data fall within an abnormality classification. For example, a user may intermittently grind his/her teeth when under stress. However, when a deviation of the user's teeth grinding exceeds a permissible threshold as compared to expected results (or falls within an abnormality classification), this may indicate bruxism and a need for medical intervention.

Various abnormal jaw movements are associated with various diseases that have unique identifiable jaw movement characteristics, which individually may be determined at perform cognitive jaw movement diagnostics 345. These unique identifiable characteristics may be detected through cognitive jaw movement diagnostics 345 performed on collected jaw movement data 325 at measurement component 320 to identify jaw abnormality 350. When properly assessed, a user's particular jaw movement pattern over time can help guide caregivers in determining appropriate treatments and preventative measures to be implemented via report component 360 through returning diagnosis and treatment recommendations 365 and/or alert doctor 370.

Jaw movement abnormalities may include, for example, rotational movement in the traverse plane, which may indicate problems with the temporomandibular joint on one side. Other abnormalities include excessive lateral jaw movement, which may indicate instability of the temporomandibular joint. Temporomandibular disorders of the jaw are often caused by problems with the jaw muscles or joints or the fibrous tissue connecting the muscles and joints. Sufferers may have headaches and tenderness of the chewing muscles or may experience clicking of the jaw joints. Jaw movement abnormalities may likewise include irregular movements caused by aftershocks from impacts (such as a car accident) as well as malocclusion and hypermobility (looseness of jaw).

Another jaw movement abnormality may be excessive movement in typical planes of jaw motion, which may suggest bruxism (teeth grinding) or muscular tension leading to stiff jaw. Jaw movement abnormalities such as chronic bruxism often result in sensitive and worn-out teeth as well as fractured, loose, decayed, and missing teeth. Enamel is often broken down and teeth are often reduced in length. White enamel is often removed to reveal soft yellow dentin, which becomes more susceptible to bacterial growth. Back teeth may have reduced cusps and biting surfaces may be impaired. Additionally, long-term bruxism physically alters an individual's appearance by moving the mandible closer to the nose, thereby receding the chin and advancing an aged look.

Data obtained from the oral monitoring device 205 may be analyzed for any of these kinds of disorders, among others, at diagnostics engine 310.

If a deviation exceeding a permissible threshold from expected results is not detected, current measurement data may be accumulated with expected results from expected results/abnormality classifications database 414 at S4 to refine expected results and abnormality classifications, further contributing to the derivation of the jaw movement pattern of the user being monitored. The accumulation of measurement data stored at S2 is linked back to S4 to allow for ongoing comparison of incoming measurement data with previously accumulated results. Further, results of database 414 may continually be refined by historical measurements of other individuals (at retrieve aggregated classifications 335), medical trials and/or research, medical professionals, and data scientists, among others.

Report component 360 of system 310, as executed by computer system/server 12, is configured to return diagnosis and treatment recommendations 365 in a report or to perform a notification procedure at alert doctor and/or user 370 when a deviation exceeding a permissible threshold is determined by health diagnostics component 330, at S5. For example, a user's jaw movement may indicate that the user suffers from a misaligned jaw. A person's normal jaw movement may be determined based on historical data. Some deviation may be expected. However, a continued misalignment greater than a predefined threshold (e.g., two percent change) may indicate an onset of a joint disease. Notification producers executed at S5 may include transmission of an alert notification (e.g., email message, text message, etc.) to a caregiver (e.g., oral healthcare professional, dentist, medical doctor, etc.) and/or to the user at alert doctor and/or user 370.

Report to an oral healthcare professional and/or to a user at report component 360 may be accomplished by any method known in the art now or hereafter. Non-limiting examples of reporting mechanisms include email, SMS text, letter, aural notification (including, for example, voice notification or sound notification), pager notification, visual notification (such as, for example, blinking lights), or any other notification. Reporting may be at regular intervals or any other interval or may be, for example, only when an anomaly is identified. A report may return diagnosis and treatment recommendations 365.

Figure 5:
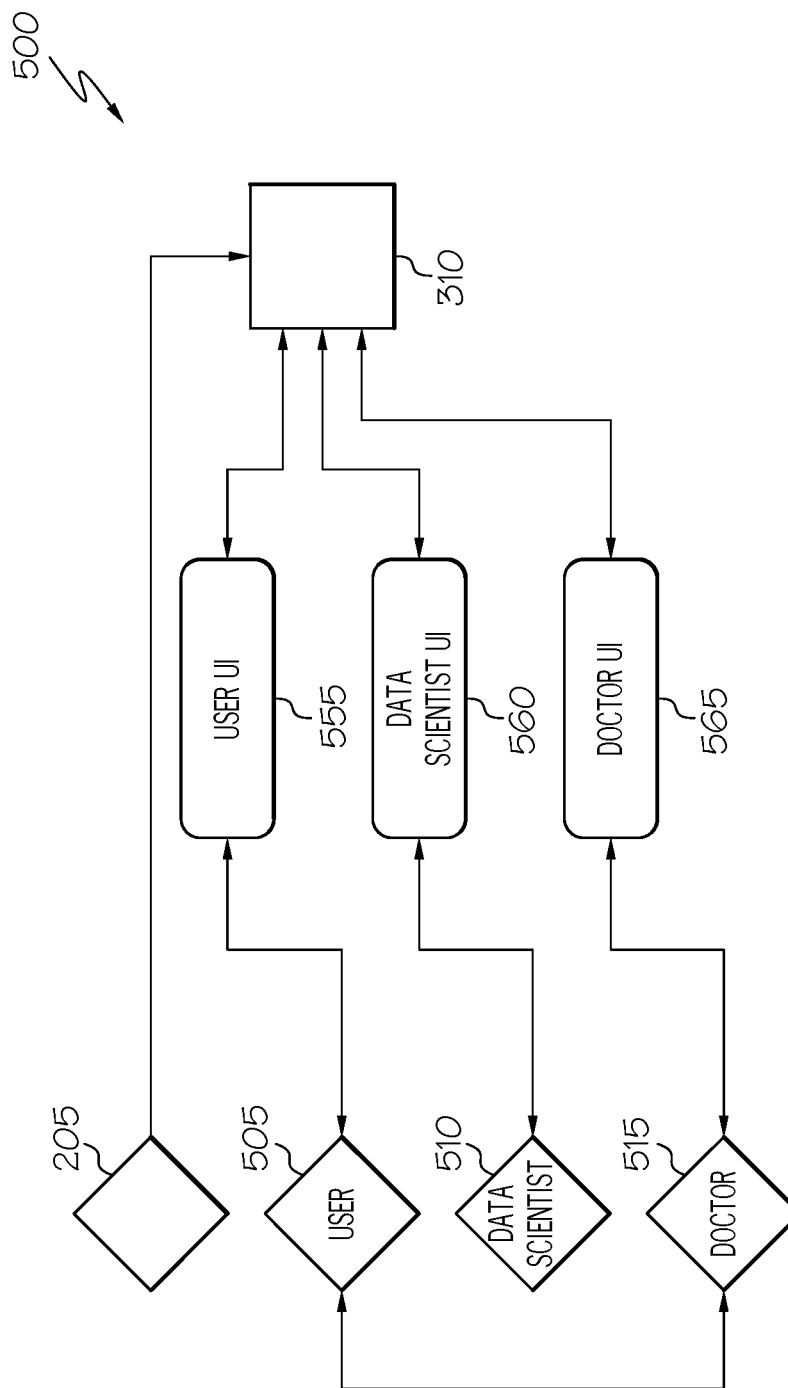
FIG. 5 shows a block diagram 500 describing the user interface functionality for displaying an oral healthcare diagnostic according to illustrative embodiments.

FIG. 5 shows a block diagram 500 describing the user interface functionality for displaying an oral healthcare diagnostic (e.g., trend, pattern, deviation, etc.) according to an embodiment of the present invention. As shown, block diagram 500 includes an oral monitoring device 205, system 310, user 505 having an electronic device with user interface (UI) 555, data scientist 510 having an electronic device with data scientist UI 560, and oral healthcare doctor (such as a dentist, hygienist, or maxillofacial surgeon) 515 having an electronic device with doctor UI 565. A suitable electronic device for communicating with system 310 may include, but is not limited to, a smart phone, a tablet computer, a laptop, and/or a desktop computer.

In a non-limiting embodiment, using user UI 555, user 505 can view the user's historical oral measurement data, any trends or patterns derived from the user's historical oral measurement data, and any feedback provided by an oral healthcare professional (e.g., doctor 515) based on the user's collected measurement data and expected results and/or abnormality classifications (e.g., improved stability of the temporomandibular joint, reduced bruxism, etc.). Using doctor UI 565, doctor 515 can view a user's historical measurement data. Based on the user's historical measurement data, doctor 515 can determine any user trends or patterns (e.g., increased instability in temporomandibular joint, increased bruxism, etc.), identify any potential oral health causes based on user patterns (e.g., jaw pain, sensitive teeth, etc.) and provide any feedback to user 505 (e.g., schedule a dental appointment, etc.). Further, doctor 515 can speculate about any potential health causes based on trends across multiple users from collected historical measurement data. Using data scientist UI 560, data scientist 510 can view measurement data of user 505 and/or others, perform any data cleansing (e.g., to be viewed by user 505 and/or doctor 515), and analyze historical measurement data to identify any trends or patterns across users.

As discussed, system 310 may perform an oral health diagnostic by comparing measurement data of a user to expected results or to jaw movement abnormality classifications. For example, Amira is informed by her oral health professional that she may be grinding her teeth. One week prior to Amira's bi-annual teeth cleaning, Amira visits her oral health professional and oral monitoring device 205 is adhered to the back of her right rear molar. Amira is provided software for program module 42 on her smart phone acting as computer system 12 that allows communication with oral monitoring device 205 and collection of data from oral monitoring device 205. For one week, Amira's jaw movement is recorded as data and stored in storage system 34.

Following the one week of data collection, Amira visits her oral health care provider for a teeth cleaning and checkup. The collected data are received by measurement component 320. Oral health diagnostic component 330 compares the current measurement data with retrieved abnormality classifications 335, identifies a possible jaw abnormality 350, and generates a report at report component 360 including diagnosis and treatment recommendations 365. Based on the comparison and historical measurement data of others as reported at 360 and the diagnosis and treatment recommendations provided at 365, doctor 515 agrees the reported trend suggests daytime bruxism. Doctor 515 recommends creation of a daytime mouth guard. Once Amira is provided with the daytime mouth guard, further measurement data is collected so that doctor 515 can determine how well the daytime mouth guard is working for her. The collected measurement data can be used to create personalized treatment plans for Amira and other users.

In another example, Eduardo is involved in a car accident and complains of a sore jaw. Oral monitoring device 205 is adhered to a rear mandibular molar to collect data. Oral monitoring device 205 collects data for one week. After one week, measurement data are received by measurement component 320. Oral health diagnostics component 330 retrieves abnormality classifications 335 and aggregated population data 340 and compares the current measurement data with classifications 335 and data 340 at perform cognitive jaw movement diagnostics 345, identifies possible jaw abnormality 350, generates diagnosis and treatment recommendations 355, and reports the diagnostics, data, and recommendations at report component 360. Based on the comparison and historical measurement data, doctor 515 notices a trend that suggests instability of the temporomandibular joint on the right side. Eduardo is treated for joint instability. His measurement data continue to be collected so that doctor 515 can determine how well any treatments for Eduardo are working. The collected measurement data can be used to create personalized treatment plans for users.

In another example, Mary has headaches. Her doctor recommends monitoring jaw movement using oral monitoring device 205. Oral monitoring device 205 is adhered to a rear mandibular molar to collect data. Mary is provided software for program module 42 on her smart phone acting as computer system 12 that allows communication with oral monitoring device 205 and collection of jaw movement data 325. Data is collected for one week and received by measurement component 320. Oral health diagnostics component 330 performs cognitive jaw movement diagnostics 345 on jaw movement data 325, abnormality classifications 335, and aggregated population data 340, and identifies tension in Mary's jaw muscles at identify jaw abnormality 350. Diagnosis and treatment recommendations are generated at 355 and reported to doctor 515 at report component 360. Doctor 515 treats Mary for jaw muscle tension. Her measurement data continues to be collected so that doctor 515 can determine how well treatments for Mary are working.

Figure 6:
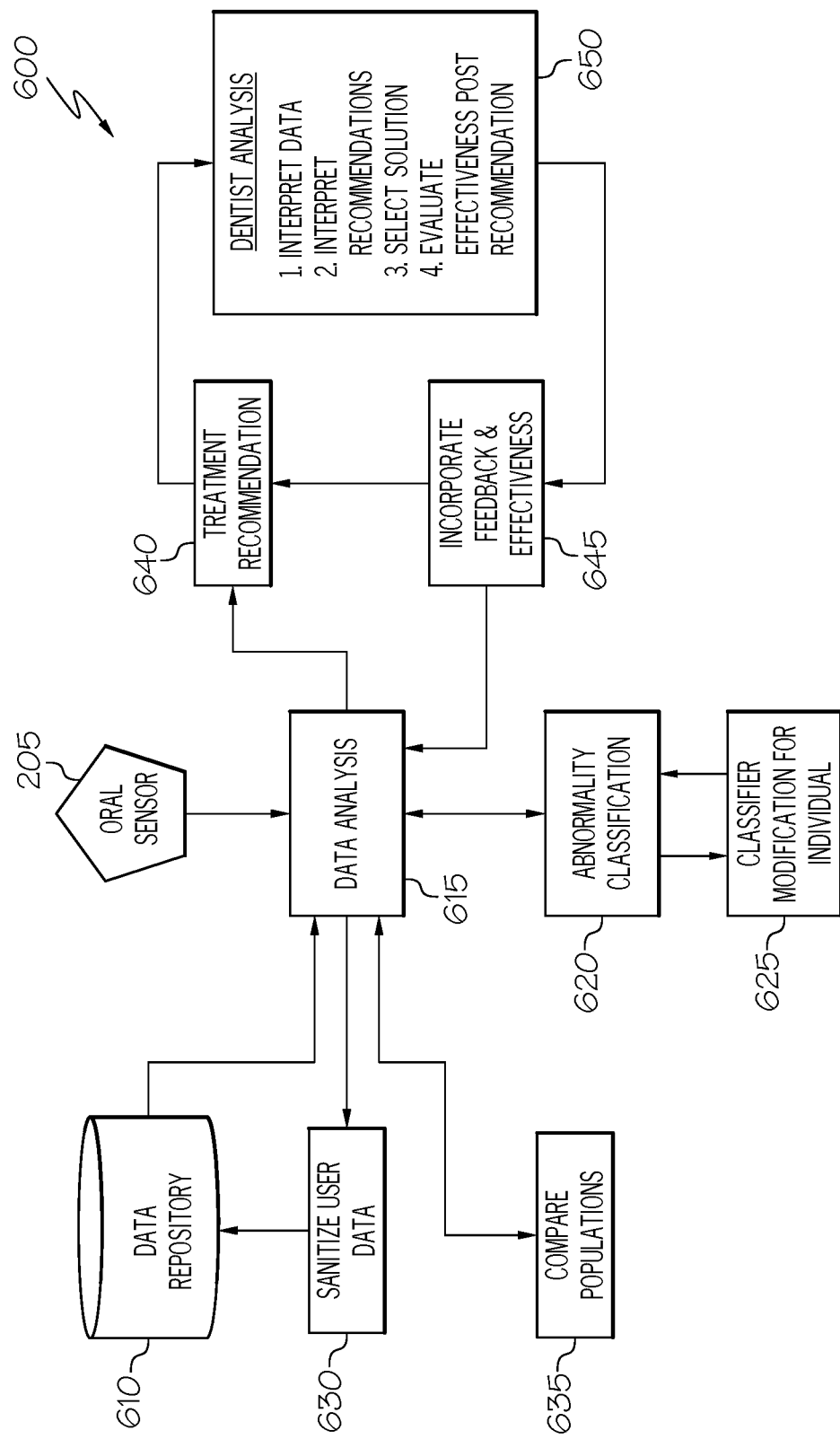
FIG. 6 shows a flow diagram 600 for performing an oral health diagnostic using an oral monitoring device to generate a treatment recommendation to an oral health care professional according to illustrative embodiments.

Referring now to FIG. 6 in conjunction with FIGS. 1-3, an example flow diagram 600 for performing an oral health diagnosis according to an embodiment of the invention is shown. Oral monitoring device 205 collects jaw movement measurement data as a user goes about daily life. As disclosed earlier, measurement data can include any objective measurements used for quantitative oral health diagnostics.

Measurement component 320 of system 310, as executed by computer system/server 12, is configured to receive any measurement data collected by oral monitoring device 205. Within diagnostics engine 310, the data pushed or pulled to measurement component 320 is analyzed in data analysis

615. Oral monitoring device data in data analysis 615 is analyzed by comparison against abnormality classification 620. Oral monitoring device data in data analysis 615 is likewise compared to at least one similarly-situated population in compare populations 635 by drawing data from data repository 610. Abnormality classification 620 is further modified for the individual data from oral monitoring device 205 in classifier modification for individual 625.

Data from oral monitoring device 205 analyzed in data analysis 615 is subject to removal of personal identifying information at sanitize user data 630 and submitted to data repository 610 for inclusion in aggregated oral health data in data repository 610. Aggregated data from data repository 610 is included in data analysis 615.

Data analysis 615 provides a treatment recommendation 640 to an oral health professional, such as a dentist. The oral health professional provides dentist analysis 650 data including interpreting data, interpreting recommendations provided at treatment recommendation 640, selecting solution, and evaluating effectiveness of solution post recommendation. Dentist analysis 650 is incorporated into treatment recommendation 640 to incorporate feedback and effectiveness 645. Incorporated feedback and effectiveness 645 is included in data analysis 615, which is sanitized via sanitize user data 630 and included in data repository 610.

As a non-limiting example, Jose has teeth missing at positions 5, 20, and 30. Jose has a bridge for those missing teeth. Jose is given an oral monitoring device 205 for one week before his bi-annual cleaning. Jaw movement data retrieved from the oral monitoring device at the bi-annual cleaning reveals a pattern of movement cognitively associated through data analysis 615 as compared to abnormality classification 620 with hypermobility. Data analysis 615 includes information concerning Jose's missing teeth and use of a bridge. Data analysis 615 compares Jose's data to sanitized user data 630 in data repository 610. Data analysis correlates Jose's jaw structure, missing teeth, use of bridge, height, weight, gender, age, etc., with a similarly-situated population at compare populations 635 and cognitively devises a treatment recommendation within a 95% confidence interval, weighted by effectiveness, based on treatments and success with similar abnormalities in the similarly-situated population. Jose's dentist is notified, and a treatment recommendation is provided to construct a newly-designed bridge along with jaw therapy. Jose's dentist analyzes the data, interprets the recommendation, selects a solution, and monitors post effectiveness by maintaining oral senor 205 in Jose's oral cavity following use of new bridge and participation in jaw therapy at dentist analysis 650. The new feedback and effectiveness data is incorporated in data analysis 615, sanitized at sanitize user data 630, and entered into data repository 610.

Data obtained as a non-limiting aspect of the present invention may be statistically analyzed for anomalies by comparison against an abnormality classification database or an expected results database. By comparison against abnormality classifications or expected results, certain types of anomalous jaw movements may be identified as indicating potential jaw pathologies. As more and more data points are collected for an individual, machine learning techniques may refine the cognitive classifier to better tell when the individual has data points that are outside of the norm for their individual data points or when the individual has data points that fall within an abnormality classification. These data may be analyzed with statistical analysis.

Data from an individual may likewise be compared against those of a similar population through aggregated crowdsourcing of data. Data collected and accumulated over time is aggregated across populations increasing accuracy of movement classification within a population and providing increased accuracy in determining abnormal movement against populations of similar age, height, gender, weight, jaw types, tooth structure, etc.

In one non-limiting embodiment, data from a population may be stored in a repository for dental information. New data from an individual may be collected in the repository after sensitive personal information is removed from the data packet. The movement data may be classified based on different variables including, for example, and not limited to, jaw shape, relative age group, height, weight, gender, etc.

In one non-limiting embodiment, statistical analysis of the variance of data points across the population and the individual is employed to identify statistically significant abnormalities of jaw movement. Acquisition of non-personal data for aggregate analysis and trending information may be used for analysis based on crowd sources. In one non-limiting embodiment, analysis of the crowd-sourced data employs a normal Gaussian distribution to derive a continuous probability distribution model. Through Gaussian distribution models, outliers and inliers in jaw movement may be identified within the distribution model.

In a non-limiting embodiment, comparison of an individual's current data against past data and/or against data from a similar population provides possible oral health diagnoses and recommendations to oral health professionals of possible root causes of jaw movement abnormalities. Analysis may provide possible causes of irregular jaw movement, possible treatment, and proactive warnings. Once outliers from expected results or inliers within an abnormality classification are cognitively identified, a medical professional may be informed of the data and may take proper action based upon analysis of the collected data.

Data aggregation to provide this analysis includes and is not limited to, for example, diagnosis and treatment recommendations made by a dentist for an individual for whom sanitized jaw movement data has been collected. Data aggregation for this analysis also includes and is not limited to, for example, a record of the results of treatment of individuals for whom data are available and for whom oral health diagnosis and treatment data are available. Failure or success of recommended treatment may be included in the data. Analysis of these data provides an output of effectiveness of treatment across a population observed to have particular jaw movement abnormalities. Similar abnormal jaw movements of similar populations are compared with that of an individual and may return diagnoses and treatments within a specified confidence interval for these abnormalities. Diagnoses and treatments may be weighted by their effectiveness.

In a non-limiting embodiment, data collected from an individual and across a population is analyzed employing cognitive data analysis. Recommendations based on existing data may be derived through the effective use of cognitive tradeoff analytics. Utilizing all data patterns for cause and effect analysis of the existing known medical mandible-based data, medical journals, and historical crowd-sourced data, an approach for recommending treatment options may be derived based on best case scenarios for patients with similar cases of jaw and mandible ailments and anomalies. As with any machine learning system, a non-limiting application provides data and training over time to recognize anomalies in data that allow high quality medical recommendations. Cognitive tradeoff analytics may be accomplished through an application-programming interface such as Watson® Tradeoff Analytics API™ (a trademark of International Business Machines Corporation of Armonk, N.Y., in the United States and/or other jurisdictions).

For cognitive analysis and machine learning, jaw abnormality classifications may be learned by the system. In general, a large number of normal and anomalous jaw movement examples are identified and labeled by one or more expert oral health professionals as normal or anomalous. A machine-learning algorithm for performing supervised learning may then allow the creation of, for example, a strong classifier out of many weak classifiers. A classifying score may then be assigned to each set of movements. A movement set having a higher score may be labeled as anomalous; a movement set with a lower score may be labeled as an expected result. Further input from oral health professionals may then allow refining of the scoring system. Extensive data and training over time allows the system to better recognize anomalies and provide higher quality medical recommendations.

Referring back to FIG. 4 and FIG. 6, process flowchart 400 and process flowchart 600 illustrate the architecture, functionality, and operation of possible implementations of systems, methods, and computer program products according to various embodiments of the present invention. In this regard, each block in the flowchart may represent a module, segment, or portion of code, which comprises one or more executable instructions for implementing the specified logical function(s). It should also be noted that, in some alternative implementations, the functions noted in the blocks might occur out of the order depicted in the Figures. For example, two blocks shown in succession may, in fact, be executed substantially concurrently. It will also be noted that each block of flowchart illustration can be implemented by special purpose hardware-based systems that perform the specified functions or acts, or combinations of special purpose hardware and computer instructions.

Some of the functional components described in this specification have been labeled as systems or units in order to more particularly emphasize their implementation independence. For example, a system or unit may be implemented as a hardware circuit that may include custom VLSI circuits or gate arrays, off-the-shelf semiconductors such as logic chips, transistors, or other discrete components. A system or unit may also be implemented in programmable hardware devices such as field programmable gate arrays, programmable array logic, programmable logic devices or the like. A system or unit may also be implemented in software for execution by various types of processors. A system or unit or component of executable code may, for instance, comprise one or more physical or logical blocks of computer instructions, which may, for instance, be organized as an object, procedure, or function. Nevertheless, the executables of an identified system or unit need not be physically located together, but may comprise disparate instructions stored in different locations which, when joined logically together, comprise the system or unit and achieve the stated purpose for the system or unit.

Further, a system or unit of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices and disparate memory devices.

Furthermore, systems/units may also be implemented as a combination of software and one or more hardware devices. For instance, program/utility 40 may be embodied in the combination of a software executable code stored on a memory medium (e.g., memory storage device). In a further example, a system or unit may be the combination of a processor that operates on a set of operational data.

As noted above, some of the embodiments may be embodied in hardware. The hardware may be referenced as a hardware element. In general, a hardware element may refer to any hardware structures arranged to perform certain operations. In one embodiment, for example, the hardware elements may include any analog or digital electrical or electronic elements fabricated on a substrate. The fabrication may be performed using silicon-based integrated circuit (IC) techniques, such as complementary metal oxide semiconductor (CMOS), bipolar, and bipolar CMOS (BiCMOS) techniques, for example. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate arrays (FPGA), logic gates, registers, semiconductor devices, chips, microchips, chip sets, and so forth. However, the embodiments are not limited in this context.

Any of the components provided herein can be deployed, managed, serviced, etc., by a service provider that offers to deploy or integrate computing infrastructure with respect to a process for performing a health diagnostic using an oral monitoring device (e.g., accelerometer) to generate a healthcare insight. Thus, embodiments herein disclose a process for supporting computer infrastructure that includes integrating, hosting, maintaining, and deploying computer-readable code into a computing system (e.g., computer system 12), wherein the code in combination with the computing system is capable of performing the functions described herein.

In another embodiment, the invention provides a method that performs the process steps of the invention on a subscription, advertising, and/or fee basis. That is, a service provider, such as a Solution Integrator, can offer to create, maintain, support, etc., a process for performing an oral health diagnosis using an oral monitoring device to generate an oral healthcare insight. In this case, the service provider can create, maintain, support, etc., a computer infrastructure that performs the process steps of the invention for one or more customers. In return, the service provider can receive payment from the customer(s) under a subscription and/or fee agreement, and/or the service provider can receive payment from the sale of advertising content to one or more third parties.

Also noted above, some embodiments may be embodied in software. The software may be referenced as a software element. In general, a software element may refer to any software structures arranged to perform certain operations. In one embodiment, for example, the software elements may include program instructions and/or data adapted for execution by a hardware element, such as a processor. Program instructions may include an organized list of commands that include words, values, or symbols arranged in a predetermined syntax that, when executed, may cause a processor to perform a corresponding set of operations.

The present invention may also be a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device, implement the functions/acts specified in the flowchart and/or block diagram block or blocks.

It is apparent that there has been provided herein approaches for performing an oral health diagnosis using an oral monitoring device to generate an oral healthcare insight. While the invention has been particularly shown and described in conjunction with exemplary embodiments, it will be appreciated that variations and modifications will occur to those skilled in the art. Therefore, it is to be understood that the appended claims are intended to cover all such modifications and changes that fall within the true spirit of the invention.

What is claimed is:

1. A computer-implemented method for identifying at least one jaw abnormality of a user comprising:
   collecting jaw movement data of the user over a period of time from an oral monitoring device affixed within the oral cavity of the user;
   retrieving a set of abnormality classifications from a database;
   performing a diagnostic of the jaw movement data by comparing the jaw movement data and the set of abnormality classifications to asses an abnormality in jaw movement; and,
   identifying a jaw abnormality of the user based on the diagnostic;
   comparing the identified jaw abnormality to similar abnormalities in jaw movements of a population of users similar to the user; and returning diagnosis and treatment recommendations within a specified confidence interval, weighted by effectiveness, based on treatments and success with the similar abnormalities in jaw movements of the population of users similar to the user.

2. The computer-implemented method of claim 1, further comprising:

performing a diagnostic of the jaw movement data by comparing the jaw movement data, the set of abnormality classifications, and jaw movement data aggregated across at least one population of users to asses an abnormality in jaw movement; and identifying a jaw abnormality using the diagnostic.

3. The computer-implemented method of claim 1 further comprising: returning diagnosis and treatment recommendations using cognitive data analysis.

4. The computer-implemented method of claim 1, further comprising generating an alert to at least one of the user and an oral healthcare professional of the user in response to identifying the jaw abnormality.

5. The computer-implemented method of claim 1, wherein the jaw movement data is data from at least one of an accelerometer and a gyroscope.

6. The computer-implemented method of claim 1, wherein the jaw movement data includes at least one of: rotational movement in the traverse plane; excessive lateral jaw movement; motion in three planes; rotational movement over an extended period of time, mandible-stroke frequency; and overall dynamic body acceleration of the jaw.

\* \* \* \* \*